(12) United States Patent
Zimbron et al.

(10) Patent No.: US 8,714,034 B2
(45) Date of Patent: May 6, 2014

(54) GAS FLUX MEASUREMENT USING TRAPS

(75) Inventors: Julio A. Zimbron, Fort Collins, CO (US); Thomas C. Sale, Fort Collins, CO (US); Mark Lyverse, Lafayette, CA (US)

(73) Assignees: Colorado State University Research Foundation, Fort Collins, CO (US); Chevron U.S.A. Inc., San Ramon, CA (US)

( * ) Notice: Subject to any disclaimer, the term of this patent is extended or adjusted under 35 U.S.C. 154(b) by 237 days.

(21) Appl. No.: 13/197,657

(22) Filed: Aug. 3, 2011

(65) Prior Publication Data
US 2013/0031955 A1 Feb. 7, 2013

(51) Int. Cl.
*G01N 1/22* (2006.01)

(52) U.S. Cl.
USPC .......... 73/863.23; 73/863; 73/864.71

(58) Field of Classification Search
USPC .............................. 73/863–864.91
See application file for complete search history.

(56) References Cited

U.S. PATENT DOCUMENTS

| | | | | |
|---|---|---|---|---|
| 2,141,261 A * | 12/1938 | Clark | | 73/864.61 |
| 2,741,921 A | 4/1956 | Windsor et al. | | |
| 3,343,421 A * | 9/1967 | Miller | | 73/864.34 |
| 3,490,288 A * | 1/1970 | Patnode | | 73/863.23 |
| 3,610,048 A * | 10/1971 | Weeks | | 73/863.23 |
| 4,065,972 A * | 1/1978 | Holub et al. | | 73/864.52 |
| 4,385,236 A * | 5/1983 | Hassib et al. | | 250/472.1 |
| 4,444,041 A * | 4/1984 | Zison | | 73/19.04 |
| 4,518,860 A * | 5/1985 | Alter et al. | | 250/253 |
| 4,700,070 A * | 10/1987 | Kovac | | 250/304 |
| 4,880,973 A * | 11/1989 | Reynolds | | 250/253 |
| 5,355,739 A * | 10/1994 | Cooper et al. | | 73/864.73 |
| 6,101,871 A * | 8/2000 | Schultz | | 73/152.25 |
| 6,598,458 B1 * | 7/2003 | Edwards et al. | | 73/19.1 |
| 6,692,970 B2 * | 2/2004 | Butnor et al. | | 436/148 |
| 7,509,836 B2 * | 3/2009 | Johnson et al. | | 73/19.01 |
| 7,704,746 B1 * | 4/2010 | White et al. | | 436/56 |
| 7,748,253 B2 | 7/2010 | Furtaw et al. | | |

(Continued)

FOREIGN PATENT DOCUMENTS

WO WO2008070922 6/2008

OTHER PUBLICATIONS

International Search Report, International Searching Authority, PCT/US12/49552, Oct. 23, 2012, pp. 1-19.

(Continued)

*Primary Examiner* — David A Rogers
(74) *Attorney, Agent, or Firm* — Samuel M. Freund; Cochran Freund & Young LLC

(57) ABSTRACT

A passive sampling apparatus and method for measuring the cumulative mass of a selected gas being transported through a known cross-sectional area, for example, a soil surface, during a chosen period of time, using absorbent material, are described. Two quantities of absorbent material are disposed in a hollow container, such as a pipe section, and spaced apart such that they may be readily separated for analysis. The absorbent material closest to the soil captures the gas leaving the soil. Under reversed flow conditions, for example when the ambient air enters the ground because of fluctuations in atmospheric pressure, the upper absorbent material captures the component of interest entering the apparatus, thereby preventing this gas from entering the lower material and disturbing the measurement. The apparatus can therefore sequester the component of interest without being affected by the direction of gas transport.

24 Claims, 4 Drawing Sheets

(56) References Cited

U.S. PATENT DOCUMENTS

| | | |
|---|---|---|
| 2009/0301234 A1 | 12/2009 | Risk |
| 2009/0314158 A1 | 12/2009 | Murphy et al. |
| 2012/0035850 A1* | 2/2012 | Risk et al. .................. 702/2 |

OTHER PUBLICATIONS

Dreimanis, A. "Quantitative Gasometric Determination of Calcite and Dolomite by Using Chittick Apparatus," J. Sedimentary Petrology, 32 (3), pp. 520-529 (1962).

J. Lodge (ed.), "Methods of Air Sampling and Analysis," 3rd Ed., Lewis Publishing Co., pp. 37-42 and pp. 678-685 (1989).

Sihota, Natasha J. et al., "CO2-Efflux Measurements for Evaluating Source Zone Natural Attenuation Rates in a Petroleum Hydrocarbon Contaminated Aquifer," Environ. Sci. Technol., 2011, 45, 482-488.

Molins, S et al., "Vadose Zone Attenuation of Organic Compounds at a Crude Oil Spill Site—Interactions between Biogeochemical Reactions and Multicomponent Gas Transport," Journal of Contaminant Hydrology, 112, 2010, 15-29.

\* cited by examiner

GAS FLUX MEASUREMENT USING TRAPS

FIELD OF THE INVENTION

The present invention relates generally to gas traps and, more particularly, to gas traps for sequestering chosen gas phase constituents crossing a known cross-sectional area over a selected period of time for later determination of the quantity thereof.

BACKGROUND OF THE INVENTION

It is known that subsurface organic contaminants and associated degradation products can occur as gas phase constituents in soil gas. In the case of releases of light nonaqueous (LNAPL) phase liquids, the mass flux of carbon dioxide ($CO_2$), a common degradation product, provides an indicator of losses of LNAPL through natural attenuation processes. Natural attenuation of LNAPL bodies can occur at rates that rival or exceed conventional LNAPL recovery technologies. In fact, NAPL losses to the gas phase by volatilization and biodegradation may be as much as two orders of magnitude larger than those due to dissolution into groundwater. Biodegradation, largely driven by methanogenesis, may overcome the dominant LNAPL mass loss process over time as the more biodegradable volatile components are quickly lost from the NAPL. Numerical modeling and field measurements using multilevel gas samplers show that degradation-generated methane can be converted to carbon dioxide relatively quickly in the subsurface, and that greater than 98% of the carbon produced by biodegradation exits the ground surface as $CO_2$.

Estimates of LNAPL losses may be used in mass balance calculations to indicate whether LNAPL bodies are stable, expanding, or shrinking, and with the relative efficiencies of the various remedial alternatives, appropriate technologies may be selected for a site.

In the case of releases of potentially stable organic contaminants, such as chlorinated solvents, the flux of stable parent compounds, for example from soil gas into indoor air (vapor intrusion), may be of importance since the risks associated with exposure to impacted indoor air can depend on the flux or contaminant loading.

Active soil gas sampling (using vacuum collection of gas samples) is presently used for rapid screening of concentrations of volatile organic compounds (VOCs) in a subsurface with moderately permeable soils. Passive sampling, which relies on diffusion and absorption, can also be used to sample for both VOCs and semi-volatile organic compounds. Tubes containing absorbent material may be placed in a sampling matrix near the surface where equilibrium has been allowed to develop between the soil gases and the sorbent over several days to weeks, and analyzed for the absorbed gas of interest, generally in a laboratory. Granular adsorbent materials in a chemically inert, hydrophobic, microporous expanded polytetrafluoroethane membrane, wherein vapors may move freely across the membrane and onto the sorbent material while water and soil are prevented from entering the sampler, have been used to identify chlorinated and aromatic vapors migrating to the surface. While passive samplers provide an indication of concentrations, they do not provide information regarding the mass of contaminants crossing a given cross-sectional area over time (contaminant flux)

Carbon dioxide efflux at the ground surface has been measured using dynamic closed chamber (DCC) method. Contaminant-related soil respiration (CSR) may be calculated from natural soil respiration (NSR) measured at background locations and total soil respiration (TSR) rates measured above LNAPL-contaminated regions. A correlation has been found between increased $CO_2$-effluxes in regions containing crude oil as determined by core analyses.

SUMMARY OF THE INVENTION

Embodiments of the present invention overcome the disadvantages and limitations of the prior art by providing a passive apparatus for cumulative (integral) measurement of the flow of a gas phase constituent through a known cross-sectional area over a known period of time (flux).

Another object of embodiments of the invention is to provide a passive apparatus for cumulative measurement of a gas constituent flowing through a known cross-sectional area over a known period of time and independent of direction of flow through the apparatus.

Yet another object of embodiments of the invention is to provide a passive apparatus for cumulative measurement of $CO_2$ gas flowing through a known cross-sectional area over a known period of time and independent of direction of flow through the apparatus.

Still another object of embodiments of the invention is to provide a passive apparatus for cumulative measurement of gas phase components of potential concern, such as benzene, perchloroethene and trichloroethene, as examples, flowing through a known cross-sectional area over a known period of time and independent of direction of flow through the apparatus.

Another object of embodiments of the invention is to provide a passive apparatus for cumulative measurement of $CO_2$ gas flowing through a known cross-sectional area over a known period of time and independent of direction of flow through the apparatus, as a LNAPL biodegradation by-product.

Yet another object of embodiments of the invention is to provide a passive apparatus for measurement of contaminant loading to a potential point of exposure, such as indoor air.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention as embodied and broadly described herein, the apparatus hereof for measuring $CO_2$ flux emanating from a subsurface source thereof, includes: a hollow container having a first opening exposed to ambient air and an opposing second opening exposed to $CO_2$ emanating from said subsurface source, a first chamber, and a second chamber in gaseous communication with the first chamber, the first chamber being in gaseous communication with the first opening of the hollow container, and the second chamber being in gaseous communication with the second opening of the hollow container; a first $CO_2$ absorbing material disposed in the first chamber and effective for permitting ambient air to flow therethrough; and a second $CO_2$ absorbing material disposed in the second chamber and effective for permitting gases including $CO_2$ emanating from the subsurface source to flow therethrough, whereby the first $CO_2$ absorbing material prevents $CO_2$ present in the ambient air from reaching the second $CO_2$ absorbing material.

In another aspect of the present invention, and in accordance with its objects and purposes, the method hereof for measuring $CO_2$ flux emanating from a subsurface source thereof, includes the steps of: providing a hollow container having a first opening exposed to ambient air and an opposing second opening exposed to $CO_2$ emanating from said subsurface source, a first chamber, and a second chamber in gaseous communication with the first chamber; permitting ambient air to flow through a first $CO_2$ absorbing material disposed in the first chamber, whereby all $CO_2$ in the ambient air flowing through the first $CO_2$ absorbing material is absorbed; permitting gases including $CO_2$ emanating from said subsurface source to flow through a second $CO_2$ absorbing material disposed in the second chamber; and quantitatively analyzing the second $CO_2$ absorbing material for absorbed $CO_2$.

In yet another aspect of the present invention, and in accordance with its objects and purposes, the apparatus hereof for measuring the flux of at least one gaseous species emanating from a subsurface source thereof, includes: a hollow container having a first opening exposed to ambient air and an opposing second opening exposed to the at least one gaseous species emanating from the subsurface source, a first chamber, and a second chamber in gaseous communication with the first chamber, the first chamber being in gaseous communication with the first opening of the hollow container, and the second chamber being in gaseous communication with the second opening of the hollow container; a first absorbing material effective for absorbing the at least one gaseous species and disposed in the first chamber and adapted to permit ambient air to flow therethrough; and a second absorbing material effective for absorbing the at least one gaseous species and disposed in the second chamber and adapted to permit gases including the at least one gaseous species emanating from said subsurface source to flow therethrough; whereby the first absorbing material prevents the at least one gaseous species from the ambient air from reaching the second absorbing material.

In still another aspect of the present invention, and in accordance with its objects and purposes, the method hereof for measuring the flux of at least one gaseous species emanating from a subsurface source thereof, includes the steps of: providing a hollow container having a first opening exposed to ambient air and an opposing second opening exposed to the at least one gaseous species emanating from the subsurface source, a first chamber, and a second chamber in gaseous communication with the first chamber; permitting ambient air to flow through a first absorbing material effective for absorbing the at least one gaseous species, and disposed in the first chamber, whereby all of the at least one gaseous species in the ambient air flowing through the first absorbing material is absorbed; permitting gases including the at least one gaseous species emanating from the subsurface source to flow through a second absorbing material effective for absorbing the at least one gaseous species, and disposed in the second chamber; and quantitatively analyzing the second absorbing material.

Benefits and advantages of embodiments of the present invention include, but are not limited to, providing an apparatus and method for passive measurement of the cumulative mass of a chosen gas flowing through a cross-sectional area for a selected time period, for example a soil surface at grade. Under reversed flow conditions, for example, when ambient air enters the ground, the upper quantity of sorbent material captures the chosen gas present in the air entering the soil, thereby preventing the chosen gas from entering the lower quantity of sorbent material and generating false measurements. The apparatus can therefore quantitatively sequester the gas without being affected by the direction of gas transport.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE INVENTION

Figure 1:
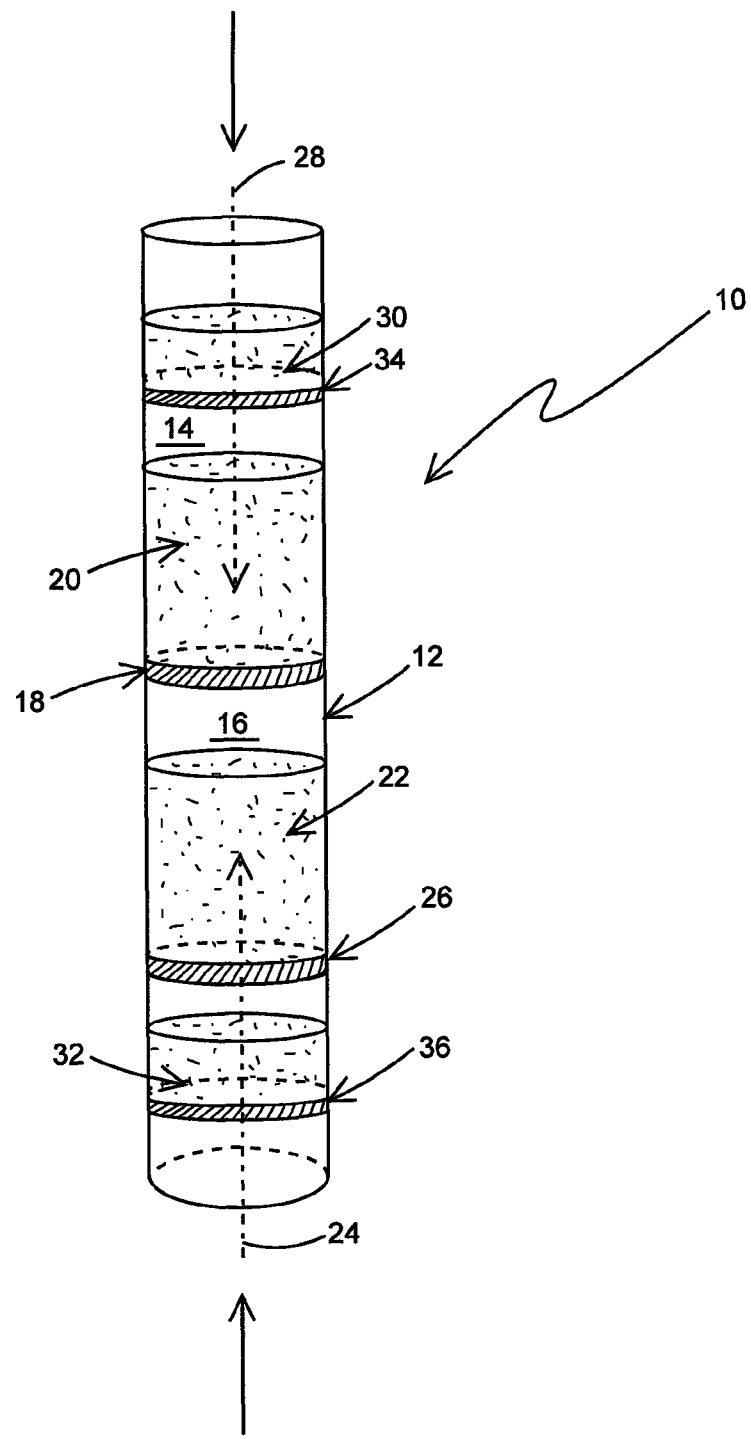
FIG. 1 is a schematic representation of a perspective side view of an embodiment of the gas trap of the invention, illustrating two quantities of gas sorbent material with optional associated dessicant disposed in a cylindrical container, the lower quantity of adsorbent material capturing the gas leaving the soil, while the upper quantity of adsorbent captures gas entering the container through the top thereof.

Briefly, embodiments of the present invention include an apparatus and method for quantifying the flux of a chosen gas being transported through a plane. The transport of gases resulting in a cumulative (integral) mass over a chosen time period divided by the cross sectional area is defined as the gas flux. As an example, a flux of $CO_2$, a natural degradation by-product of LNAPL is measured at a plane, typically at grade, above the LNAPL, using $CO_2$ passive adsorption traps. Other examples include measurements of the flux of benzene, perchloroethene and trichloroethene. It is anticipated that for petroleum hydrocarbons such as benzene, that measurements may advantageously made in the vicinity of the water table, that is, below grade. In what follows, the discussion will be directed to flux measurements of carbon dioxide as the gaseous species of interest.

Carbon dioxide is present in atmospheric air in significant quantities. Therefore, the sorption of $CO_2$ from soils must be differentiated from that present in the air. Two chambers containing $CO_2$-absorbing material, depending on the application, are utilized to achieve this differentiation: an upper chamber captures and sequesters all atmospheric $CO_2$ gas entering the trap (from diffusion and temporary gradients due to atmospheric pressure changes); and a lower chamber captures and sequesters $CO_2$ entering the trap from the soil.

Cylindrical receivers, for example, tubes, are installed to about a foot below ground surface with the upper portion thereof above the surface. As stated, two quantities of gas-sorbent material are disposed in a hollow container, such as a pipe section, adapted to mate with the receivers. The quantities of sorbent material are spaced apart such that they may be readily separated for analysis. The sorbent material closest to the soil captures the gas leaving the soil. Under reversed flow conditions, for example, when the ambient air flows into the ground as a result of atmospheric pressure changes, the upper absorbent material captures the component of interest flowing into the container in the ambient air, thereby preventing this gas from entering the lower material and disturbing the measurement. The apparatus can therefore sequester the component of interest without being affected by the direction of gas transport. Gas collection is conducted over a chosen time period, after which the traps are collected and analyzed after transport to a laboratory, as an example. Depending on the ambient moisture, optional layers of dessicant, such as silica gel, can be added to the traps.

State of the art measurements use instant concentration measurements in addition to estimates or measurements of total gas flow, which require intensive processing before a flux may be determined. By contrast, the cumulative measurements of gas components of embodiments of the present invention may occur over days or weeks, and are less sensitive to short-term fluctuations, which are in the order of less than 1 day, thereby yielding a measurement of gas flux, which avoids the need for transport models.

For $CO_2$ measurements, trap receivers were installed in previously dug holes, and the inner volume of the receivers were re-packed to original grade with excavated native material. A concrete seal around each receiver was allowed to set overnight before installing the trap canisters. Uninstalled traps were used as travel blanks.

Reference will now be made in detail to the present embodiments of the invention, examples of which are illustrated in the accompanying drawings. In the FIGURES, similar structure will be identified using identical reference characters. Turning now to FIG. 1, a schematic representation of a side projection view of an embodiment of gas-trap, 10, of the present invention is illustrated. Hollow, cylindrical tube, 12, is divided into upper chamber, 14, and lower chamber, 16, by metal or plastic screen, 18, which permits gases to flow in either direction while keeping upper porous adsorbent material, 20, in place. Lower chamber 16 contains $CO_2$ or other gas adsorbent material, 22, effective for capturing the gas being released from the ground into the atmosphere, 24, and held in place by metal or plastic screen, 26. Upper chamber 14 adsorbs the same gas from ambient air, 28, due to diffusion and/or due to barometric pumping (that is, sudden increases in atmospheric pressure driving gases into the soil).

In humid environments, porous desiccant materials, 30, and 32, such as silica gel as an example, held in place using porous screens, 34, and 36, respectively, and disposed as shown, may be added to chambers 14 and 16, respectively. The various gas-absorbing and dessicant materials may be held apart using a gas porous material such as glass wool.

Figure 2:
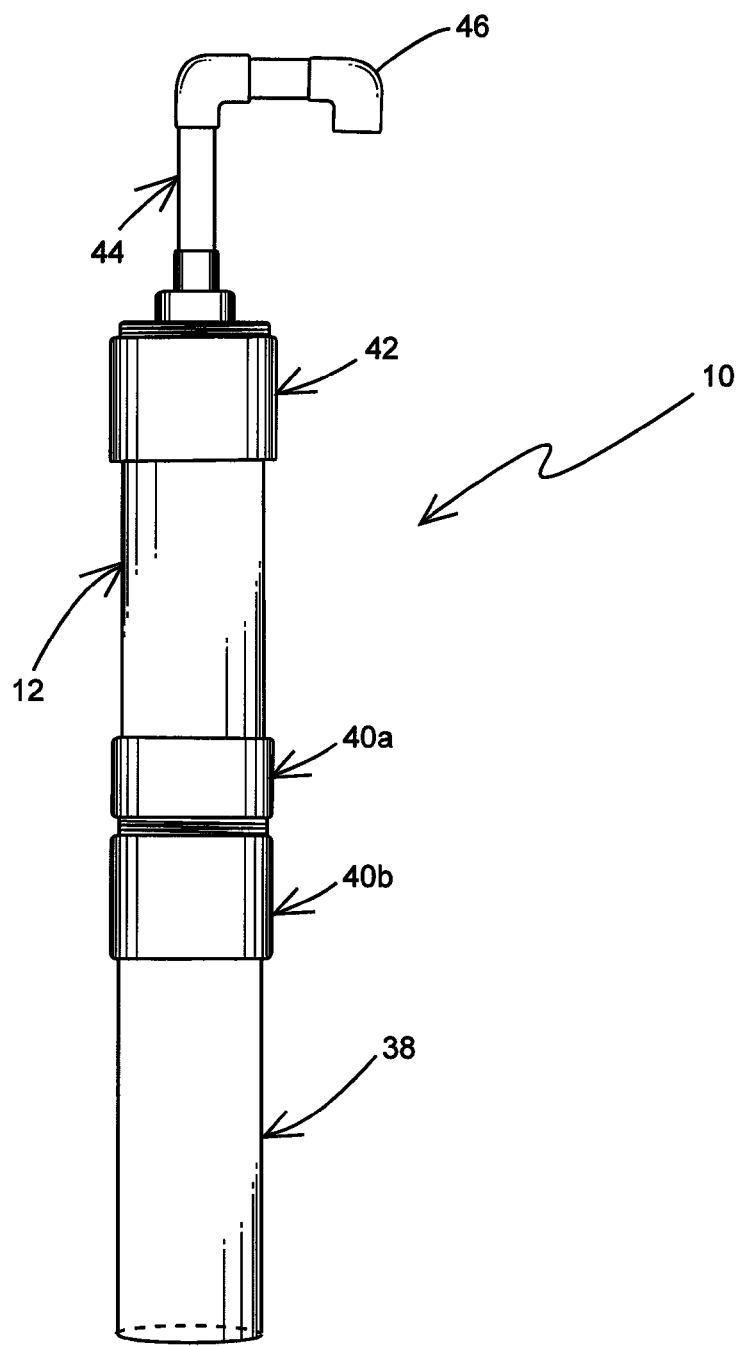
FIG. 2 is a schematic representation of a perspective side view of the container shown in FIG. 1 hereof, illustrating the lower end thereof in gaseous communication with a field-receiver buried in the soil, which permits gases exiting the soil to flow through the container, and the upper end thereof in gaseous communication with a downward-opening pipe to reduce the quantity of water entering the container while permitting atmospheric gases to flow through the container.

FIG. 2 is a schematic representation of a perspective view of trap 10 shown in FIG. 1 hereof illustrating attachment of the trap to trap receiver, 38, pre-installed in the ground, using air-tight, detachable, O-ring fittings, 40a, and 40b. The traps were constructed using 4" OD PVC pipe, and protected from rain using detachable cap, 42, having fitting, 44, and inverted pipe section, 46, attached thereto.

Figures 3A, 3B, 3C:
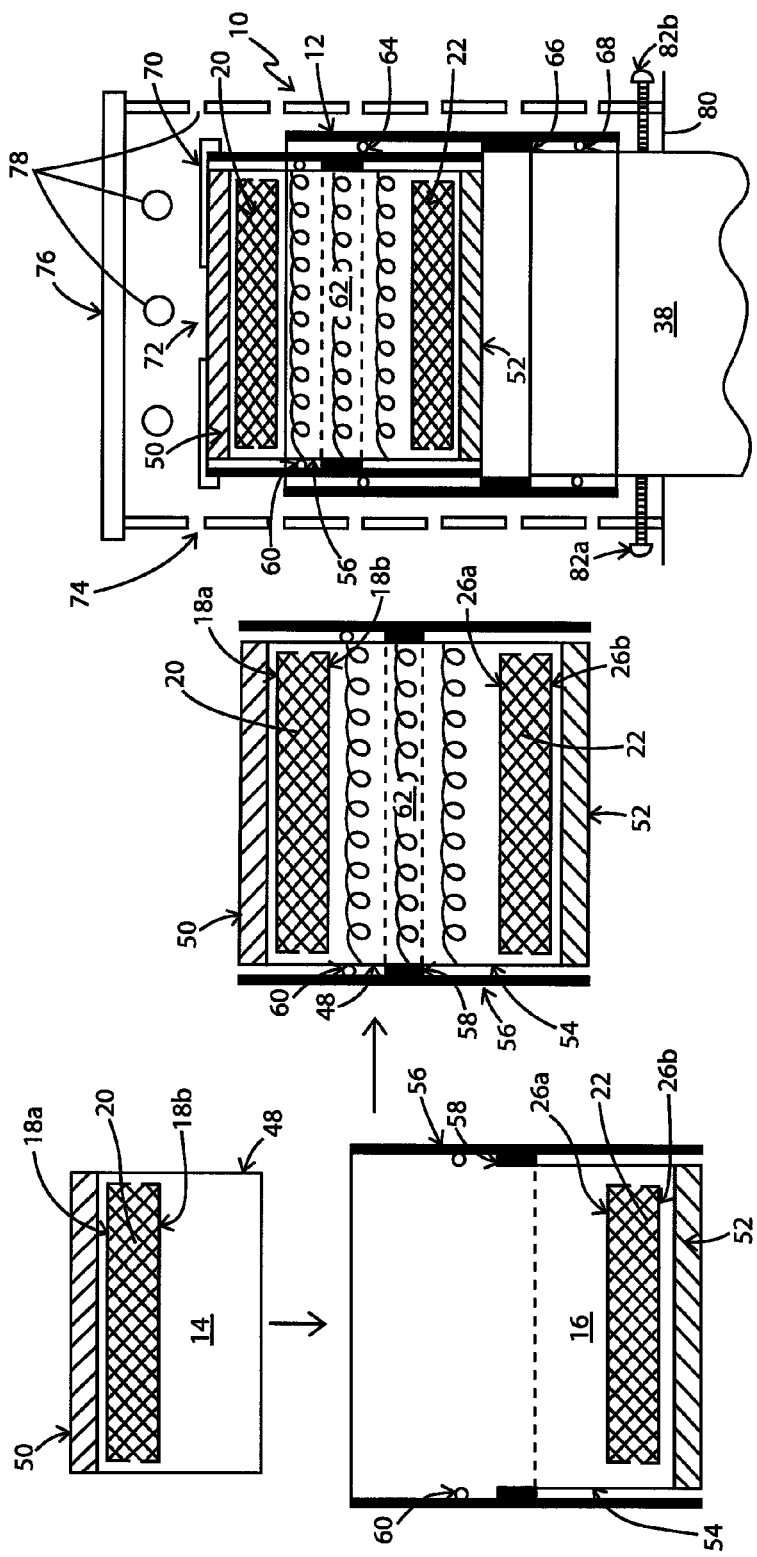
FIGS. 3A-3C illustrate a schematic representation of a side view of another embodiment of the gas trap of the present invention.

In another embodiment of the present gas trap illustrated in FIGS. 3A-3C hereof, upper chamber 14 includes a plastic tube, 48, to the top of which slotted cap, 50, is glued or otherwise attached for holding upper mesh screen 18a in place, while permitting gases to freely flow therethrough. Mesh screens 18a and 18b, confine gas absorbing material 20 to a region therebetween. Lower chamber 16 has a similar construction, where slotted cap, 52, is glued or otherwise attached to the bottom of plastic tube, 54, which holds lower mesh screen 26b in place, while permitting gases to freely flow therethrough. The slots in caps 50 and 52 may be of any size or design, as long as screens 18a and 26b are supported, respectively, and the gas flowing therethrough is substantially unrestricted. Mesh screens 26a and 26b confine gas absorbing material 22 to a region therebetween. Mesh screens 18 and 26 may be fabricated from metal, such as stainless steel, or from plastic, as examples. As stated, the screens permit unrestricted gas flow while retaining the absorbent material, especially during shipping and deployment, and ensure an approximately even medium thickness. Absorbent media are likewise chosen to provide as small a restriction to gas flow as is practicable. Tube 54 is inserted is inserted into the lower portion of larger cylindrical tube, 56, and the upper portion of tube 54 is glued or otherwise sealably attached to insert, 58, which is sealably attached around the circumference of the inside surface of larger cylindrical tube, 56. Tube 48 is removably inserted into the upper portion of larger tube 56, wherein it is sealed by O-ring, 60, disposed in a circumferential groove in the inner surface of tube 56, and supported by insert 58. The space between lower mesh screen 18b and upper mesh screen 26a in upper and lower chambers 14 and 16, respectively, may be filled with a gas permeable material, 62, such as glass wool.

Larger tube 56 is adapted to reversibly fit into cylindrical tube 12, wherein it is sealably contacted by O-ring, 64, disposed in a circumferential groove in the inner surface of tube 12, and stopped and supported by insert, 66, circumferentially disposed on the inner surface of tube 12. Receiver 38 is adapted to be fitted into the lower portion of tube 12, wherein it is stopped and supported by insert 66 and reversibly sealably attached to tube 12 by O-ring 68 disposed in a circumferential groove in the inner surface thereof. This permits tube 12 to be readily installed in the field and removed for analysis. Tube 12 is fitted with cover, 70, having a hole, 72, therein for permitting gases to freely pass therethrough, and covered by rain shield, 74, having solid cover, 76, to block rain, and numerous holes, 78, therein to permit free passage of gases into the region of hole 72 in cover 70. Hole 72 in cover 70 serves to reduce diffusive atmospheric gas flux from reaching the absorbent material by reducing the cross-sectional area for diffusion. Typically, a 1-in. diameter hole may be used for a 4-in. diameter cover. Rain shield 74 is supported on the ground surface, 80, through which receiver 38 passes, and may be attached to receiver 38 using circumferentially placed plastic screws or metal screws covered by rubber boots to avoid damaging the plastic receivers, 38, screws 82a and 82b, being shown as examples. This permits rain shield 74 to be removed from gas trap 10. If desiccants are required, they may be accommodated in upper and lower chambers, 14 and 16, respectively, in a similar manner to that illustrated in FIG. 1 hereof.

In use, after removal of rain shield 74 from trap 10, and removal of tube 12 from receiver 38, upper tube 48 may be removed from tube 56 for emptying the absorbing materials for analysis, and for cleaning and filling. Once inverted, the contents of the upper tube 48 may be removed by removing lower screen 18b, after which absorbent material 20 may be collected for analysis. After cleaning and, if necessary, replacement of screen 18a, new absorbent material may be added and secured by placing screen 18b over this material. A similar process may be used to collect for analysis, clean, and fill lower chamber 16, with the exception that tube 54 is not removed from tube 56. Field receiver 38 may be tapered above ground surface to facilitate connection with tube 12.

After field deployment for $CO_2$ measurements, the traps were analyzed using a gasometric analysis method described in "Quantitative Gasometric Determination of Calcite by Using Chittick Apparatus" by A. Dreimanis, J. Sedimentary Petrology, 32 (3), pages 520-529 (1962) as follows.

The basis for trapping $CO_2$ from gases onto solid media (which includes a small amount of sorbed water) is the water/air partitioning equilibrium, and the subsequent equilibrium of $CO_2$ with carbonic acid (in aqueous solution):

$$CO_{2(gas)} \leftrightarrow CO_{2(aq.)} \quad \text{Equation 1; and}$$

$$CO_{2(aq.)} + H_2O \leftrightarrow H_2CO_3 \quad \text{Equation 2.}$$

If a base (for example, sodium hydroxide, NaOH) is present in the aqueous medium, neutralization of the carbonic acid occurs in accordance with:

$$H_2CO_3 + 2NaOH \leftrightarrow H_2O + Na_2CO_3 \quad \text{Equation 3.}$$

A moisture-resistant mixture of bases (calcium and sodium hydroxides, as an example) may be coated onto silicates to achieve a high surface area, and follow the above series of reactions. More particularly, silicate material coated with sodium hydroxide, and granulated to a size between 4 and 12 mesh may be found in the commercial sorbents Ascarite or Decarbite, which rely on the above series of reactions.

Once $CO_2$ is sequestered as $Na_2CO_3$ in the solid media, the solid media is removed from the traps, weighed, dissolved in a known volume of deionized water, and analyzed based on a method developed for the quantification of carbonates in soils (typically in the form of calcite and dolomite, calcium and magnesium carbonates, respectively). Analysis of the traps consists of acidification in a closed system, and collection of the evolved $CO_2$ at constant pressure. Analysis may be conducted on both bottom and top elements of the trap, one measuring $CO_2$ fluxes out of the ground and another one measuring fluxes into the ground, respectively, to verify that neither has exceeded its sorption capacity. Blank measurements on laboratory and travel blanks are used to correct field measurements. The measurement on a background (non-impacted) location may also be used to compare with the non-background measurements (that is, in areas presumably impacted).

The volume of $CO_2$ produced by reacting carbonates with a strong acid is determined. The change in pH from strongly basic to strongly acidic reverses the sequences of reactions shown in Equations 1-3:

$$Na_2CO_3 + 2HCl \leftrightarrow 2NaCl + H_2CO_3 \leftrightarrow CO_{2(aq.)} \leftrightarrow CO_{2(gas)}.$$

Figure 4:
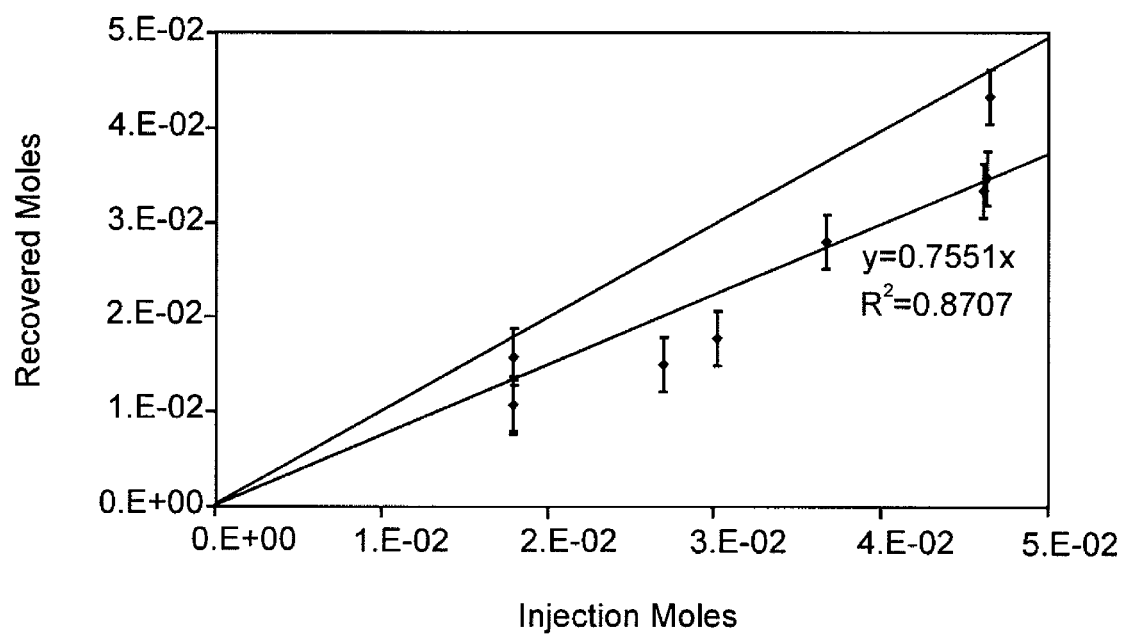
FIG. 4 is a graph showing recovery of $CO_2$ as a function of the amount of carbonate injected into $CO_2$ traps illustrated in FIG. 1 hereof under laboratory conditions, the slope indicating an average recovery of about 75%.

A Chittick apparatus was used to analyze the resulting $CO_2$, where the fluid soltrol was used in the leveling reservoir to increase the resolution of the readings, due to the lower density of soltrol with respect to water. As shown in FIG. 4, a calibration curve using known amounts of sodium carbonate (from injection of known quantities of $CO_2$ into Ascarite in the trap illustrated in FIGS. 3A-3C hereof under laboratory conditions) gave an $R^2$ value of 0.87 with a linear response up to the equivalent of about 0.075 g of $CO_2$, or approximately 0.18 g of sodium carbonate. The data indicates an average recovery of between 75% and 85%. In the field, $CO_2$ flux results may be reported in micromoles per square meter per second ($\mu mol/m^2 \cdot s$).

The method detection limit (MDL) may be estimated to be approximately equal to 5 times the standard deviation of a low-level blank. Fourteen analyses of travel blanks resulted in an average of about 0.2 mM of $CO_2/g$ of sorbent Ascarite, with a standard deviation of approximately 0.12 mM $CO_2/g$ of Ascarite. This yields a detection limit of about 0.4 mM of $CO_2/g$ of Ascarite (or approximately 0.17 mg of $CO_2/g$ of Ascarite). A laboratory blank was constructed in the same fashion as the field traps, and was analyzed before trap field installation to establish baseline concentrations in the media. These laboratory blanks were subtracted from actual field measurements to account for small amounts of $CO_2$ initially adsorbed onto the Ascarite. Non-blank readings were typically between 1 and 3 times higher than those for the travel blanks.

Some $CO_2$ absorbent materials are sensitive to moisture (for example, Decarbite, Ascarite, both containing NaOH immobilized on silicates). If these materials absorb too much water, they lose physical integrity. As stated hereinabove, one solution is to use desiccants such as silica gel. A moisture resistant mixture of hydroxides called SodaSorb used for scuba diving rebreathers is an alternative. SodaSorb has a sorption capacity of approximately 0.3 g of $CO_2/g$ of SodaSorb. Sofnolime is also moisture resistant formulation of calcium hydroxide. The highest $CO_2$ fluxes measured at field sites by the present inventors are in the order of 10 micromole/$(m^2 \cdot sec)$ which is equivalent to 2.66 g of $CO_2/(m^2 \cdot week)$. Traps having an internal diameter of 4 in. were loaded with approximately 50 g of SodaSorb, and typically deployed for 2 weeks. This is a conservative field deployment time since the material sorption capacity at the above-mentioned measured fluxes would require at least 7 weeks in the field before saturation occurs.

Saturation of either the top or bottom traps would result in unsequestered $CO_2$ affecting the other trap, yielding an unreliable measurement. Therefore, after each analysis, the $CO_2$ absorption of both top and bottom traps is compared to the maximum sorption capacity of the material used (that is, about 0.3 g of $CO_2/g$ of sorbent material, for SodaSorb) to verify that saturation has not occurred.

The two-chamber trap illustrated in FIGS. 1 and 2 may also be used to measure the flux of contaminants by replacing the strong-base sorbents for $CO_2$ with sorbents such as activated carbon or the polymeric material Tenax (poly-2,6-biphenyl phenylene oxide), as examples, suitable for absorbing volatile organic compounds (VOCs), such as benzene or chlorinated hydrocarbons, as examples. Recovery of the sorbed contaminants may be by extraction using the solvent carbon disulfide ($CS_2$) when using activated carbon, or by thermal desorption of the Tenax followed by standard gas chromatographic (GC) analysis. Details of air sampling methods, typically using active air pumps to determine concentration of contaminants in air, as opposed to flux measurements, may be found in *Methods Of Air Sampling and Analysis* $3^{rd}$ Ed. by J. Lodge (ed.), Lewis Publishing Co., page 763 (1989).

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. An apparatus for measuring $CO_2$ flux emanating from a subsurface source thereof, comprising:
   a hollow container having a first opening exposed to ambient air and an opposing second opening exposed to $CO_2$ emanating from said subsurface source, a first chamber, and a second chamber in gaseous communication with the first chamber the first chamber being in gaseous communication with the first opening of said hollow container, and the second chamber being in gaseous communication with the second opening of said hollow container;

a first $CO_2$ absorbing material disposed in the first chamber and adapted to permit ambient air to flow therethrough; and a second $CO_2$ absorbing material disposed in the second chamber and adapted to permit gases including $CO_2$ emanating from said subsurface source to flow therethrough;

whereby said first $CO_2$ absorbing material prevents $CO_2$ from the ambient air from reaching said second $CO_2$ absorbing material.

2. The apparatus of claim 1, further comprising a receiving tube having a first open end and an opposing second open end in gaseous communication with the second chamber at one open end thereof, and adapted for partial burial in the ground such that the second open end thereof is exposed to $CO_2$ emanating from said subsurface source thereof.

3. The apparatus of claim 2, further comprising a gas tight-coupling for reversibly sealably connecting the first open end of said receiving tube with said second chamber.

4. The apparatus of claim 1, further comprising a first gas permeable screen between said first $CO_2$ absorbing material and said second $CO_2$ absorbing material, and a second gas permeable screen between said second $CO_2$ absorbing material and the second opening of said container.

5. The apparatus of claim 1, further comprising a cap sealably connected to said container at the first opening thereof, said cap having a hole therein with a chosen diameter for permitting gases to flow therethrough.

6. The apparatus of claim 5, further comprising a rain shield.

7. The apparatus of claim 5, further comprising a section of tubing having a first end in gaseous communication with the hole in said cap, and a second end facing said subsurface source for preventing rain from entering the hole.

8. The apparatus of claim 1, further comprising a first desiccant material disposed in the first chamber between the first opening thereof and the first $CO_2$ absorbing material; and a second desiccant material disposed in the second chamber between the second $CO_2$ absorbing material and the second opening.

9. The apparatus of claim 1, wherein said first $CO_2$ absorbing material and said second $CO_2$ absorbing material comprise at least one hydroxide.

10. The apparatus of claim 9, wherein said first $CO_2$ absorbing material and said second $CO_2$ absorbing material are immobilized.

11. A method for measuring $CO_2$ flux emanating from a subsurface source thereof, comprising the steps of:

providing a hollow container having a first opening exposed to ambient air and an opposing second opening exposed to $CO_2$ emanating from the subsurface source, a first chamber, and a second chamber in gaseous communication with the first chamber;

permitting ambient air to flow through a first $CO_2$ absorbing material disposed in the first chamber, whereby all $CO_2$ in the ambient air flowing through the first $CO_2$ absorbing material is absorbed;

permitting gases including $CO_2$ emanating from the subsurface source to flow through a second $CO_2$ absorbing material disposed in the second chamber; and quantitatively analyzing the second $CO_2$ absorbing material for absorbed $CO_2$.

12. The method of claim 11, wherein the first $CO_2$ absorbing material and the second $CO_2$ absorbing material comprise at least one hydroxide.

13. The method of claim 12, wherein the first $CO_2$ absorbing material and the second $CO_2$ absorbing material are immobilized.

14. The method of claim 11, further comprising the step of preventing water vapor from reaching the first $CO_2$ absorbing material and the second $CO_2$ absorbing material.

15. An apparatus for measuring the flux of at least one gaseous species emanating from a subsurface source thereof, comprising:

a hollow container having a first opening exposed to ambient air and an opposing second opening exposed to said at least one contaminant emanating from said subsurface source, a first chamber, and a second chamber in gaseous communication with the first chamber the first chamber being in gaseous communication with the first opening of said hollow container, and the second chamber being in gaseous communication with the second opening of said hollow container;

a first absorbing material effective for absorbing said at least one gaseous species and disposed in the first chamber and adapted to permit ambient air to flow therethrough; and a second absorbing material effective for absorbing said at least one gaseous species and disposed in the second chamber and adapted to permit the at least one gaseous species emanating from said subsurface source to flow therethrough;

whereby said first absorbing material prevents said at least one gaseous species present in the ambient air from reaching said second absorbing material.

16. The apparatus of claim 15, further comprising a receiving tube in gaseous communication with the second chamber at one open end thereof, and adapted for partial burial in the ground such that the second open end thereof is exposed to gases from said subsurface source thereof.

17. The apparatus of claim 16, further comprising a gas tight-coupling for reversibly sealably connecting the first open end of said receiving tube with the second chamber.

18. The apparatus of claim 15, further comprising a first gas permeable screen between said first absorbing material and said second absorbing material, and a second gas permeable screen between said second absorbing material and the second opening of said container.

19. The apparatus of claim 15, further comprising a cap sealably connected to said container at the first opening thereof, said cap having a hole therein with a chosen diameter for permitting gases to flow therethrough.

20. The apparatus of claim 19, further comprising a rain shield.

21. The apparatus of claim 19, further comprising a section of tubing having a first end in gaseous communication with the hole in said cap, and a second end facing said subsurface source for preventing rain from entering the hole.

22. The apparatus of claim 15, wherein said first absorbing material and said second absorbing material are chosen from activated carbon and poly-2,6-biphenyl phenylene oxide.

23. A method for measuring the flux of at least gaseous species emanating from a subsurface source thereof, comprising the steps of:

providing a hollow container having a first opening exposed to ambient air and an opposing second opening exposed to the at least one gaseous species emanating from the subsurface source, a first chamber, and a second chamber in gaseous communication with the first chamber;

permitting ambient air to flow through a first absorbing material effective for absorbing the at least one gaseous species, and disposed in the first chamber, whereby all of the at least one gas species in the ambient air flowing through the first absorbing material is absorbed;

permitting gases including the at least one gaseous species emanating from the subsurface source to flow through a second absorbing material effective for absorbing the at least one gaseous species, and disposed in the second chamber; and quantitatively analyzing the second absorbing material for the absorbed at least one gaseous species.

24. The method of claim 23, wherein the first at least one absorbing material and the second at least one absorbing material are chosen from activated carbon and poly-2,6-biphenyl phenylene oxide.

* * * * *